(12) United States Patent
Ribnicky et al.

(10) Patent No.: US 6,348,220 B1
(45) Date of Patent: Feb. 19, 2002

(54) PHENETHYLISOTHIOCYANATE NUTRACEUTICAL COMPOSITIONS AND METHODS

(75) Inventors: David M. Ribnicky, Plainsboro; Alexander A. Poulev, Highland Park; Ilya Raskin, Manalapan, all of NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/289,015

(22) Filed: Apr. 9, 1999

(51) Int. Cl.[7] ............................................. A61K 35/78
(52) U.S. Cl. .................... 424/725; 424/755; 424/776
(58) Field of Search .............................. 424/195.1, 725, 424/755, 776

(56) References Cited

PUBLICATIONS

Chung–Wen Chen, et al. Analysis of thermal Degradation Products of Allyl Isothiocyanate and Phenethyl Isothiocyanate. In: ACS Symposium Series 705:152–163. *American Chemical Society*. 1997.

Jed W. Fahey, et al. Broccoli sprouts: An exceptionally rich source of inducers of enzymes that protect against chemical carcinogens. *Proc. Natl. Acad. Sci. USA*. 1997 94:10367–10372.

Victor Gil and Alexander J. MacLeod. Degradation of Glucosinolates of *Nasturtium Officinale* Seeds. *Pytochemistry*. 1980 19:1657–1660.

Victor Gil and Alexander J. MacLeod. Some Glucosinolates of Farsetia Aegyptia and Farsetia Ramosissima. *Pytochemistry*. 1980 19:227–231.

Victor Gil and Alexander J. MacLeod. Studies on Degradation in *Lepidium Sativum* Seed Extracts. *Pytochemistry*. 1980 19:1369–1374.

Stephen S. Hecht, et al. Effects of Watercress consumption on Metabolism of a Tobacco–specific Lung Carcinogen in Smokers. *Cancer Epidemiology, Biomarkers & Prevention*. 1995 4:877–884.

Usha Palaniswamy, et al. Supplemental Light before Harvest Increases Phenethyl Isothiocyanate in Watercress under 8–hour Photoperiod. *HortScience*. 1997 32(2) :222–223.

Artturi I. Virtanen. Studies on Organic sulphur compounds and other Labile Substance in Plants. *Phytochemistry*. 1965 4:207–228.

Carol L. Zrybko, et al. Determination of Glucosinolates in Domestic and Wild Mustard by high–Performance Liquid Chromatography with Confirmation by Electrospray Mass Spectrometry and Photodiode–Array Detection. *Journal of Chromatography A*. 1997 767:43–52.

*Primary Examiner*—Francisco Prats
*Assistant Examiner*—Susan D. Coe
(74) *Attorney, Agent, or Firm*—Marshall, Gerstein & Borun

(57) ABSTRACT

The present invention provides methods for obtaining phenethyl isothiocyanate (PEITC), a natural glucosinylate derivative, from plant tissue. The methods involve selection of plant tissue naturally rich in PEITC, followed by aqueous extraction under conditions that promote optimal release of PEITC from the tissue. The invention further provides plant preparations containing significant quantities of PEITC and nutraceutical formulations comprising these preparations.

24 Claims, 3 Drawing Sheets

PHENETHYLISOTHIOCYANATE NUTRACEUTICAL COMPOSITIONS AND METHODS

FIELD OF THE INVENTION

This invention relates to the field of pharmaceutically active or otherwise beneficial compounds obtained from natural sources. In particular, the invention provides a seed preparation enriched in phenethyl isothiocyanate, a naturally-occurring anticancer and cancer preventative substance.

BACKGROUND OF THE INVENTION

Various scientific articles are referred to in parentheses throughout the specification, and complete citations are listed at the end of the specification. These articles are incorporated by reference herein to describe the state of the art to which this invention pertains.

Most people are familiar with the biting taste of horseradish and mustard, the pungent flavors of cabbage and Brussels sprouts and the peppery sensation of watercress. These plants belong to a broad group of species consisting of the Cruciferae and fourteen other families, which contain over 100 related natural chemical compounds, called glucosinolates, which are responsible for the familiar flavors and aromas of these plants. Plants that contain glucosinolates are widely consumed by people and livestock. The occurrence and biochemistry of glucosinolates has been well-documented. The variation in glucosinolate content among these plants is tremendous. Some plants can contain predominantly one form of glucosinolate while others are characterized by as many as fifteen different forms.

Glucosinolates are nitrogenous natural products that are derived from one of several different amino acids. Glucosinolates also contain sulfur from cysteine as well as a molecule of glucose, which is attached by a thioglucosidic bond. Many plants contain very high concentrations of glucosinolates, which presumably serve a protective function (Mithen, 1992). When plant tissues are disrupted, the glucosinolates rapidly break down into one of several forms. The first step of this breakdown is catalyzed by a class of enzymes generally referred to as myrosinases. The unstable aglycone which results from the removal of the glucose moiety by the myrosinase then rearranges into one of three basic forms by a process which is generally spontaneous. The basic forms that result from this rearrangement are either isothiocyanates, nitrites or thiocyanates. The wide variety of forms of glucosinolates and their breakdown products results from a biosynthetic pathway that originates from different amino acids, followed by subsequent modifications, all of which seem to be species specific. Although glucosinolates have been the focus of intensive research, many aspects of this diverse biochemical system have yet to be resolved.

Vegetables that contain glucosinolates have long been known to be a healthy part of the daily diet. For instance, the isothiocyante, sulforaphane, has been shown to be a powerful cancer preventive compound that specifically induces phase II detoxification enzymes (Zhang et al., 1992). Sulphoraphane is one example of several isothiocyanates that are characterized by similar kinds of health benefits. PEITC (phenethyl iosthiocyanate) is a glucosinolate breakdown product which is similar to sulforaphane and has also been a focus of intensive cancer preventive research. In addition to the extensive research done with animal systems, PEITC from fresh watercress has been shown to specifically inhibit the oxidation of nitrosamines from tobacco in human smokers as measured by urinary excretion of metabolites (Hecht et al., 1995). PEITC has been repeatedly shown to be both an effective and stable cancer preventive and anticancer compound. Not only does it inhibit the carcinogenic activation of many of the components of tobacco products, but prevents similar effects of many other toxins as well as even promote the death of cancerous cells.

The health promoting and anticancer benefits of PEITC may be obtained by consuming large amounts of the vegetables that are rich in this substance. However, such consumption may not be practical or desirable. It would be preferable if PEITC could be obtained in a more concentrated form such that its benefits could be enjoyed, for instance, through daily consumption of a small capsule, rather than large amounts of PEITC-containing vegetables.

SUMMARY OF THE INVENTION

In accordance with the present invention, plant varieties and specific tissues have been identified that are rich natural sources of PEITC, and methods have been devised to increase the production of PEITC in these tissues and to obtain preparations of certain plant tissues that are highly enriched in PEITC.

According to one aspect of the present invention, a preparation of disrupted plant tissue, comprising at least 1 mg PEITC per gram fresh weight of the plant tissue, is provided. Preferably, the preparation comprises at least 5 mg PEITC per gram fresh weight plant tissue, and most preferably at least 10 mg PEITC per gram fresh weight plant tissue. In a preferred embodiment, the preparation is made from seeds of upland cress, and may be provided as a dried product.

According to another aspect of the invention, a nutraceutical formulation is provided, which comprises the plant tissue preparation described above.

A preferred embodiment of the present invention provides a crushed, dried preparation of upland cress seed, comprising at least 5 mg PEITC per gram dry weight. A nutraceutical formulation also provided, comprising this preparation.

According to another aspect of the present invention, a method is provided for obtaining a plant tissue preparation that contains at least 1 mg PEITC per gram fresh weight of the tissue. The method comprises: (a) providing fresh or fresh-frozen plant tissue; (b) disrupting the tissue; and (c) incubating the disrupted tissue in an aqueous solution for a time and at a temperature effective to produce the preparation that contains at least 1 mg PEITC per gram fresh weight of the tissue. In one embodiment, the disrupted tissue is incubated in water, a method preferred when the tissue is incubated at slightly elevated temperature, e.g., 30° C. In another embodiment, the disrupted tissue is incubated in a biologically compatible buffer. Preferably, the pH of the disrupted tissue in the aqueous solution is between 4.0 and 8.0, more preferably between 4.5 and 7.2.

In the aforementioned method, the incubation is performed at a temperature between 20° C. and 37° C., more preferably between 27° C. and 32° C., and most preferably at 30° C. The incubation is performed for at least 2 minutes and preferably between 10 and 40 minutes, most preferably for 20 minutes.

It is preferred that the aforementioned method be practiced on upland cress seeds. It is also preferred that the seeds are frozen in liquid nitrogen before disruption. After disruption, the plant material may be subjected to freeze-drying, preferably to a final temperature of less than 10° C., more preferably to 0° C.

According to another aspect of the invention, a plant tissue preparation comprising at least 1 mg PEITC per gram fresh weight plant tissue, prepared by the aforementioned method, is provided.

According to a specific aspect of the present invention, a method of obtaining a preparation of upland cress seed containing PEITC is provided. The method comprises: (a) providing fresh or fresh-frozen upland cress seed; (b) crushing the seeds; and (c) incubating the seeds in an aqueous solution at 30° C. for 20 minutes. The method may further comprise freeze-drying the preparation to a final temperature of 0° C. A PEITC-containing upland cress seed preparation, prepared by the aforementioned method, is also provided, as is a nutraceutical formulation for prevention or treatment of cancer, which comprises the upland cress seed preparation.

Other features and advantages of the present invention will be better understood by reference to the drawings, detailed description and examples that follow.

DETAILED DESCRIPTION OF THE INVENTION

Figure 1:
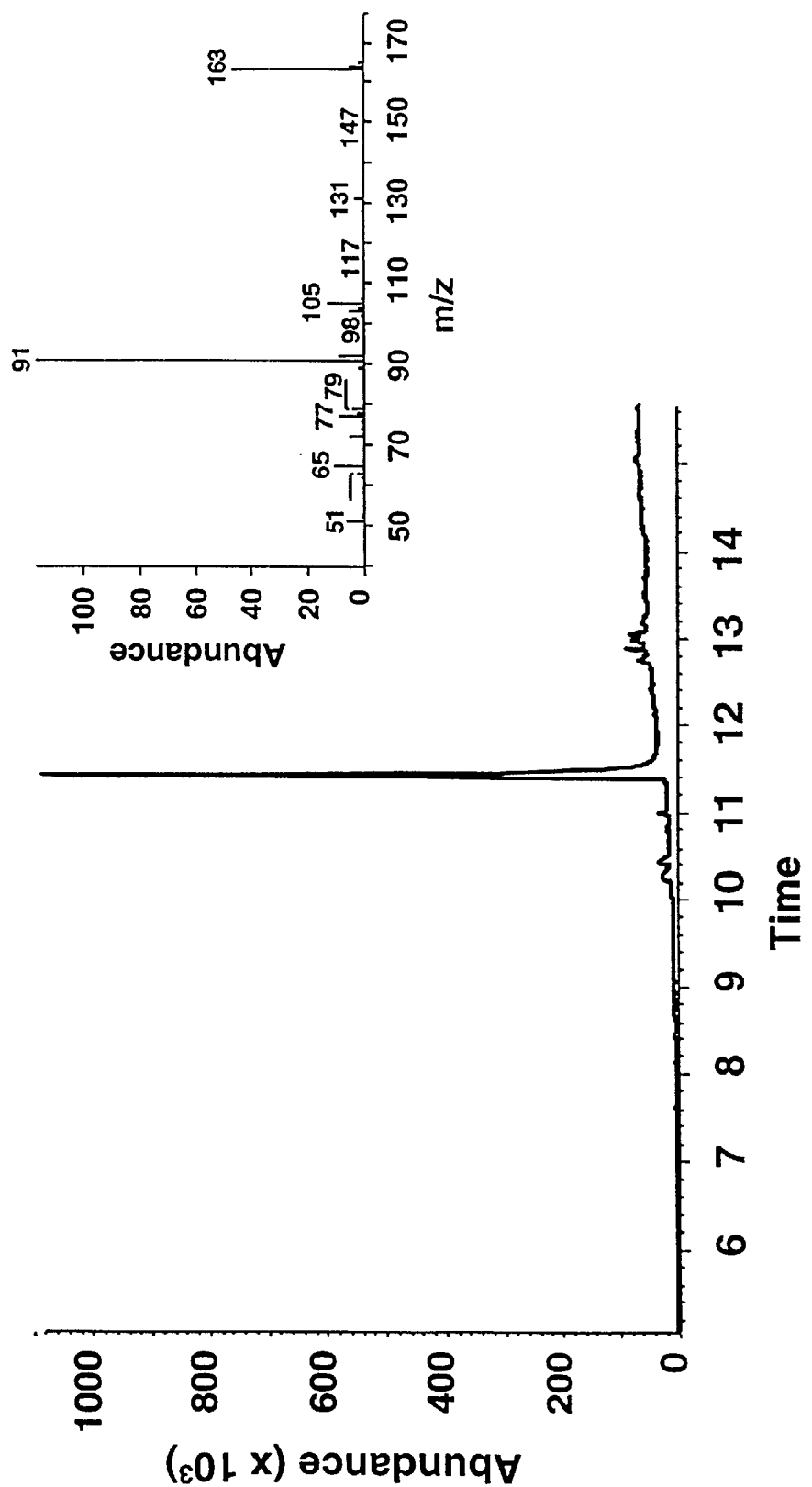
FIG. 1. Gas chromatograph and mass spectrum (shown as inset figure) of PEITC from upland cress seed after standard treatment as described in Example 1.

The release of isothiocyanates from glucosinolates has been commonly observed in cruciferous vegetables, which are known to offer substantial health benefits. PEITC has been shown specifically to be an important anticancer and cancer preventive agent in various experimental systems. Time, temperature and pH are factors known to influence glucosinolate degradation, but a pragmatic investigation of the production of PEITC from various plant species and the conditions influencing PEITC production heretofore had not been performed. The present inventors have systematically investigated (1) the occurrence and amounts of PEITC in several plant species and in specific tissues, and (2) factors influencing the release, accumulation and recovery of PEITC from selected plant material.

In accordance with the present invention, it has been found that the seed of upland cress provides the greatest potential source of PEITC, and methods have been devised to ensure maximal release of PEITC from upland cress (*Barbarea verna*) seeds, yielding processed seed meal containing as much as 2% (on a dry weight basis) of the desired product. Freeze-drying of the wetted seed meal yields a dried form appropriate for commercial processing with a high recovery of product which is stable over time.

The description below exemplifies upland cress (also referred to as winter cress), particularly the seeds, as the plant and tissue of choice for obtaining significant quantities of PEITC. However, it will be appreciated by persons skilled in the art that the same methods could be applied to any PEITC-containing plant species, with an expectation of obtaining PEITC in high proportion to whatever amount is contained within that species.

Thus, the inventors have developed a method for obtaining high yields of PEITC from plant sources, particularly upland cress seeds. In its most basic form, the method comprises the following steps: (1) provide fresh or fresh-frozen plant material; (2) optionally, freeze the tissue in liquid nitrogen; (3) grind or otherwise macerate the tissue in an aqueous solution; and (4) incubate the wetted tissue at a slightly elevated temperature (e.g., 30° C.) for several minutes, which promotes optimum release of PEITC. Water may be removed from the tissue by freeze drying. Details of the protocol are set forth below.

Using the aforementioned procedure on upland cress seeds, a dried seed preparation is obtained which contains between about 1 and 20 mg PEITC per gram fresh weight starting material. The determination of the amount of PEITC in a plant tissue preparation is made as set forth in Example 2: the crushed plant material (subjected to the treatment set forth above or to some comparative treatment) is extracted with a suitable solvent, e.g., ethyl acetate, then subjected to chromatographic or mass spectral analysis. By way of comparison, upland cress seeds which are directly extracted with solvent release very little PEITC (about 12 µg/gfw tissue), whereas upland cress seeds subjected to the methods of the present invention yield in the range of 1,000 fold more PEITC (1–20 mg or more per gfw) due to the optimization of conditions that favor release of the PEITC from the tissue.

As mentioned, the plant species chosen for obtaining PEITC plays a very important role in how much PEITC can be obtained from the plant source. Upland cress contains a high concentration of PEITC. However, other plant species also contain significant amounts of these compounds, and could be used instead of upland cress as a plant source of PEITC. These include various members of the cruciferae, and related genera, particularly watercress. However, upland cress exceeds any of these plant species in PEITC content.

As mentioned, the PEITC content in upland cress also varies with the tissue type. Seeds contain the highest concentration of PEITC. Leaves have been reported to produce as much as 6.7 mg PEITC per gram dry weight tissue (Palaniswamy et al., 1997); however, since leaf tissue has about a ten-fold more higher water content than does seed tissue, this number extrapolates to about 0.67 mg PEITC per gram fresh weight of tissue. Accordingly, seeds are preferred for use in the present invention, but leaves or other plant parts may be used. For instance, an alternative embodiment utilizes the entire plant as a convenient source of PEITC.

Plant tissue, preferably seed, is ground or otherwise macerated, preferably after freezing with liquid nitrogen. The macerated tissue is then wetted with a small volume of aqueous solution, preferably at a ratio of at least 1:1 (w:w) liquid to plant material, more preferably 1:2 (larger volumes of liquid may be used, but results in increased drying time in embodiments where the preparation is dried). In a preferred embodiment, the aqueous solution is water. In alternative embodiments, the aqueous solution may be a buffer, such that the pH of the wetted plant material may be adjusted. The pH of wetted upland cress seed in water is about 4.5. Optimum release of PEITC was found to occur at pH 7.2 at 22° C., therefore a preferred embodiment of the invention comprises use of a buffer for wetting the plant material, to achieve the higher pH in embodiments using the lower temperature.

The wetted plant material is then incubated for an appropriate time and at an appropriate temperature to effect maximum release of PEITC. Preferably, the wetted plant material is incubated for at least two minutes, more preferably 10 to 40 minutes, and most preferably about 20 minutes, at a temperature between about 20° C. and 37° C., more preferably between 27° C. and 32° C. and most preferably about 30° C. Temperature is an especially significant factor affecting release of PEITC from plant tissue. As can be seen by referring to FIGS. 3, 4 and 5, release of PEITC from upland cress seeds was greatest after incubation at 30° C., at pH ranges from 4.5 (the pH of the mixture when incubated with water) to 7.2. By comparison, at an incubation temperature of 22° C., the release of PEITC from upland cress seeds was less, but a pH effect was observed.

Following the incubation, the macerated tissue is reduced to dryness to produce a residue highly enriched in PEITC. The inventors have found that lyophilization to a final temperature of 0° C. to, e.g., 10° C., results in recovery of a residue containing significant amounts of intact PEITC, e.g. up to 2% based on the dry weight of the residue.

Following the specific steps recited above, a particularly preferred embodiment of the invention utilizes the following steps, which are described in detail in Example 2: (1) grind upland cress seeds in liquid nitrogen; (2) wet the seeds in an aqueous solution, preferably water; (3) incubate the wetted seed mixture at 30° C. for 20 minutes; and (4) lyophilize the seed preparation to a final temperature of 0° C.

The dried PEITC-containing plant preparations can be tabletted or encapsulated or otherwise formulated for oral administration. The formulations preferably are administered as a dosage unit of PEITC. The term "dosage unit" refers to a physically discrete unit of the preparation appropriate for a patient undergoing treatment or using the compound for prophylactic purposes. Each dosage unit contains a quantity of active ingredient, in this case PEITC, calculated to produce the desired effect in association with the selected formulation. Preferred dosages of PEITC range from 10–50 mg as a daily dose for an average adult human.

Nutraceutical formulations of PEITC prepared as described above are useful for general health benefits and for prevention or treatment of a variety of diseases or other detrimental conditions. For instance, as mentioned earlier, PEITC may be administered for treatment or prevention of cancer. PEITC also may be administered to prevent deleterious effects of environmental toxins or pollutants, or their formation in the body, inasmuch as it has been shown to prevent oxidation of certain toxins into more toxic forms.

The following examples are provided to describe the invention in greater detail. They are intended to illustrate, not to limit, the invention.

EXAMPLE 1

Analysis of Watercress and Upland Cress for Phenethyl Isothiocyanate Content Methods Two grams of fresh leaf material was ground in liquid nitrogen and extracted in 20 mL of water. One mL was removed, cleared of particulates by centrifugation at 10,000 g for 10 min in a 13×100 mm test tube and partitioned 2 times with 2 mL ethyl acetate:cyclopentane:2-propanol (100:99:1). The organic mixture was then reduced to 1 mL in vacuo and analyzed by GC-MS. The samples were manually injected in the splitless mode into a gas chromatograph (model 5890, Hewlett-Packard) /mass spectrometer (model 5971, Hewlett-Packard) equipped with a 30-m×0.25 mm DB-5MS fused silica capillary column (J&W Scientific, Folsom Calif.). Chromatographic parameters were as follows: injection temperature at 150° C., initial oven temperature at 50° C. for 5 min followed by a ramp at 30° C. min to 280° C. for 3 min. The MS was operated by scanning from 50 to 650 (m/z). The retention time of PEITC was 11.3 min which appeared as the primary metabolite using this technique (see FIG. 1). The major ion of PEITC has a mass of 91 (m/z) (FIG. 1) which was used as the basis for the calculation of the concentration of PEITC within the sample by comparison with corresponding standards of known concentration. Standard curves were constructed across a broad range of PEITC concentrations. These concentrations were also verified using the molecular ion of mass 163 (m/z) of the sample and standard. These conditions were used for all subsequent analyses and standards were used to verify instrument linearity on a daily basis. All measurements consisted of the average of at least 3 replicate samples injected with the same sample volume.

Results Several glucosinolates have been measured in various species and within specific plant structures such as leaves, seeds, flowers, pods and roots. Watercress (*Nasturtium officinale*) and upland cress (*Barbarea verna*) are know for the presence of gluconasturtiin, a common glucosinolate which releases PEITC. Concentrations of PEITC in watercress leaf tissue were shown to increase from 3.0 to 6.7 mg/g DW with the modification of temperature and photoperiod (Palaniswamy et al., 1997). Seeds of upland cress were shown to contain high concentrations of gluconasturtiin (Zrybko et al., 1997) reaching several percent. Our initial investigations of watercress and upland cress showed that upland cress contained about 200 µg/g FW of PEITC, which was at least 20% more PEITC than found in watercress. It was not determined, however, if this PEITC was present as a free form or released from gluconasturtiin during sample preparation.

Broccoli seedlings have been well-documented as a rich source of sulforaphane, the isothiocyanate of that crucifer (Fahey et al., 1997). Our initial investigations of seed showed that watercress seed contained about 7 fold lower concentrations of PEITC than did upland cress seed while the seedlings from each appeared to contain dilutions thereof.

EXAMPLE 2

Standard Processing of Seed to Obtain a Preparation Enriched in PEITC

Initial protocols for obtaining PEITC from seed comprised grinding the seed in liquid nitrogen, followed by solvent extraction. These conditions may not have precluded the release of PEITC from the cold seed meal which may have condensed moisture from the air. Results of preliminary experiments indicated that the release of PEITC from upland cress tissue after tissue disruption began within minutes. It has been previously shown that the release of PEITC can occur at low temperatures (Gil and MacLeod, 1980a,b,c). Direct grinding and extraction of upland cress seed into ethyl acetate showed that the concentration of free PEITC was only about 12 µg/g FW. The protocol described below resulted in an increase of about 1000-fold in PEITC content in upland cress seed.

Methods

One gram of seed was ground in liquid nitrogen with a mortar and pestle and transferred to a 50 mL plastic conical centrifuge tube. The seed material was then wetted with 2 mL of pure water, capped and incubated at 30° C. for 20 min. The treated seed meal was then partitioned into 5 mL of ethyl acetate, transferred to a 13×100 mm test tube and centrifuged at 10,000 g for 10 min at 4° C. A portion of the ethyl acetate fraction was then either directly injected or diluted 50 times followed by GC-MS analysis as described above. Such modifications of the analytical techniques were necessarily made in response to the higher concentrations of PEITC achieved within the samples. For time course experiments, the incubation time was extended to both 40 and 60 min while the incubation temperature was maintained at room temperature (22° C.). For experiments investigating the effects of pH on the release of PEITC, pure water was replaced with 2 mL of 200 mM phosphate buffer, pH 7 or 200 mM phosphate buffer pH 8 which produced a pH of treated seed mixtures of 6.8 and 7.2 respectively. The pH of the seed mixture in pure water was 4.5. A solution of 200 mM sodium bicarbonate solution was also used for the treatment of the seed meal and yielded a final pH of 7. The release of PEITC after the 20 min incubation was also measured at 22° C. and 37° C. In addition, experiments with the combinations of the variables which influence the release of PEITC were performed in order to determine which conditions were optimal for the release of PEITC from the wetted seed. Similar experiments were performed with leaf tissue as well as 3-day-old seedlings grown in the dark for 3 days at 22° C. Most experiments were performed with upland cress, which was determined to be the richest source of PEITC release. Some experiments were performed with watercress plants, seed and seedlings for comparative purposes.

The process of lyophilization (freeze-drying) was used to remove the water from the treated seed meal in some of the experiments. Lyophilization was performed in a Vitris Genesis 12ES freeze dryer which removed the water from the processed samples with vacuum starting at a temperature of −50° C. followed by slow warming to a final temperature of either 26° C. or 0° C. Lyophilization to a final temperature of 26° C. or 0° C. took approximately 2 or 3 days respectively. Samples to be analyzed after lyophilization were then rewetted with 2 mL of water and processed using the standard method described above.

The stability of PEITC was investigated in seed meal kept in the dark at 22° C. Five grams of seed for each treatment were processed as described above, lyophilized to 0° C. and placed into either a capped or open 50 mL centrifuge tube. The samples were reground with a mortar and pestle after lyophilization to ensure homogeneity. On days 4, 7, 10 17 and 25, 100 mg from each treatment was processed as described above, with the omission of the final dilution of ethyl acetate. On day 68, the measurement of PEITC was performed using 1 gram from each treatment and processed as described above for the 1 gram samples.

Results

Figure 2:
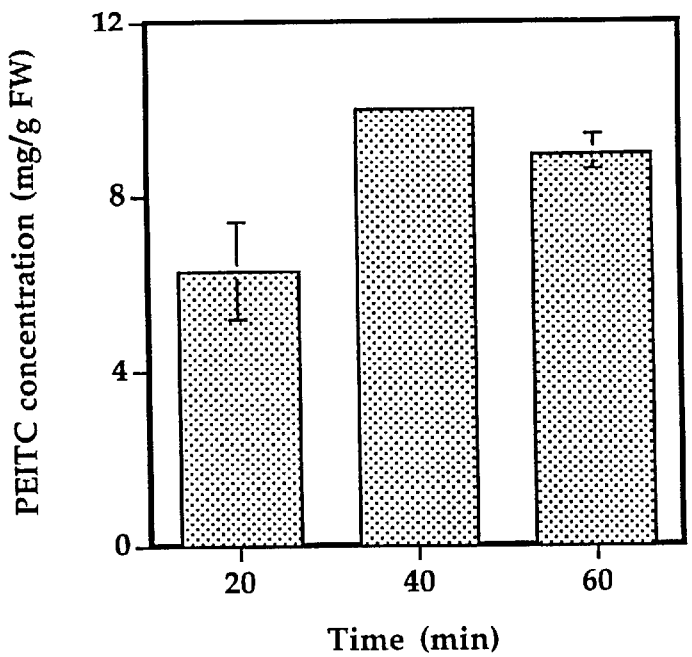
FIG. 2. The effect of incubation time on the release of PEITC from water-treated seed meal maintained at 22° C. All values are given ± standard error.

The effect of incubation time on the release of PEITC from water-treated seed meal maintained at 22° C. is shown in FIG. 2. Since the release of PEITC was determined to occur rapidly, the release of PEITC from seed meal was measured at 20, 40 and 60 minutes prior to solvent extraction. The optimal time for the release of PEITC in pure water at room temperature (22° C.) was about 40 min. PEITC degradation may begin to occur after extended incubation times.

Figure 3:
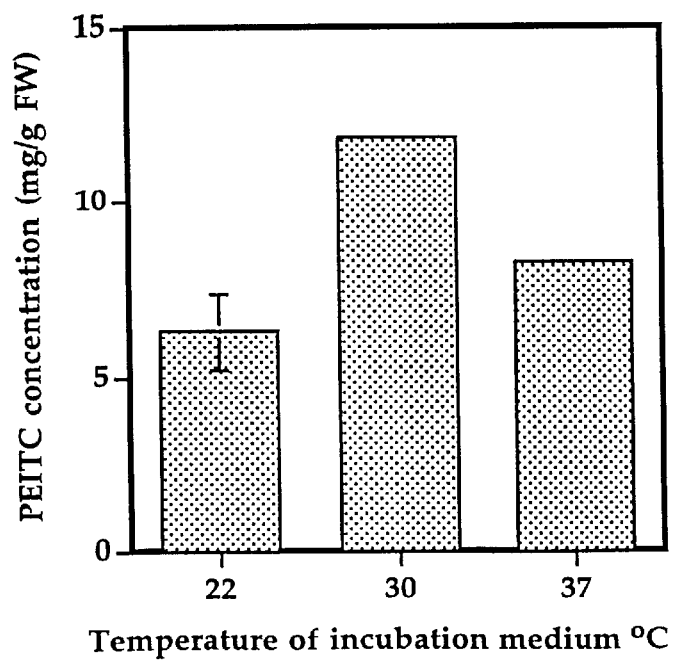
FIG. 3. The effect of temperature on the release of PEITC from water-treated seed meal during a 20 min incubation period. All values are given ± standard error.

FIG. 3 shows the effect of temperature on the release of PEITC from water-treated seed meal during a 20 minute incubation period. Temperature has been a well-documented factor which can influence the accumulation of glucosinolate breakdown products (Virtanen, 1964). The breakdown of glucosinlolates occurs as a two step process, both steps of which could be differentially influenced by temperature. FIG. 3 shows that at 37° C., more PEITC was released than at 22° C. while the maximum amount of PEITC was released at an incubation temperature of 30° C. Temperatures higher than 30° C. may not only have a negative influence on the release of PEITC but may also promote further degradation and loss of PEITC. PEITC has been shown, however, to be stable under conditions analogous to the cooking of cruciferous vegetables (Chen et al., 1998)

Figure 4:
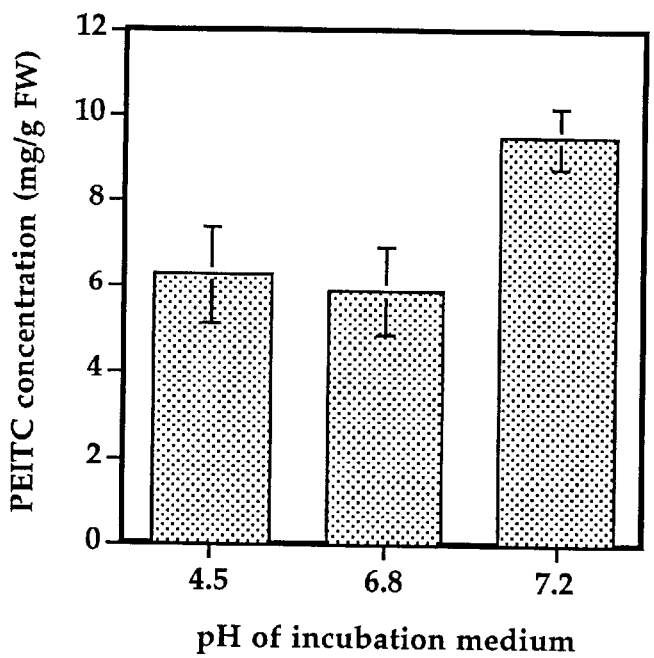
FIG. 4. The effect of pH on the release of PEITC from treated seed meal incubated for 20 min at 22° C. All values are given ± standard error.

The effect of pH on the release of PEITC from treated seed meal incubated for 20 min at 22° C. is shown in FIG. 4. As with temperature, the pH of damaged or macerated tissues can have a profound effect on the release and accumulation of glucosinolate breakdown products. Considerable variation in the effects of pH have been reported in the literature, but this variation appears to correlate with species and glucosinolate diversity. FIG. 4 shows that the final pH of the seed mixture did influence the release of PEITC from ground seed meal after 20 min of exposure at 22° C. Similar amounts of PEITC were released at pH 4.5 which resulted from the addition of pure water and at pH 6.8 after the addition of phosphate buffer with a pH of 7. At pH 7.2, however, which resulted from the addition of phosphate buffer pH 8, the release of PEITC was significantly elevated. Somewhat improved results were obtained using a sodium bicarbonate solution which yielded a final pH of 7. This buffer was investigated for practical reasons of eventual mass production as an herbal supplement to be consumed. These results contradict some of the earlier literature which describes the formation of the isothiocyanates to be promoted at a pH of less than 5 (Virtanen, 1964) but is supported by more current literature which agrees with the data presented above (Gil and MacLeod, 1980b). In studies with *Lepedium sativum*, the pH range of 6.69–7.42 was observed to have a negligible effect on the products released during autolysis (Gil and MacLeod, 1980c).

Figure 5:
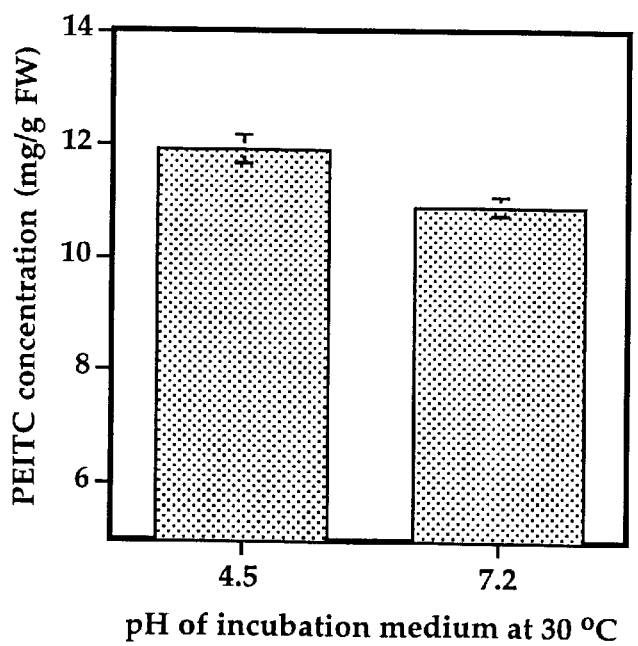
FIG. 5. The effect of pH on the release of PEITC incubated for 20 min at 30° C. All values are given ± standard error.

FIG. 5 shows the effect of pH on the release of PEITC incubated for 20 min at 30° C. Since the most dramatic increases in the release of PEITC were observed after 20 min at a pH of 7.2 or at a temperature of 30° C., these conditions were combined in order to determine whether pH or temperature was the more dominant factor influencing the release of PEITC or if there was a synergistic effect of both factors. These results clearly demonstrated that the temperature of the incubation medium was the most important factor and that the elevated temperature promoted even greater release of PEITC at the pH which was not optimal at 22° C. Other experiments were also performed showing that at 30° C., longer incubation times or the use of sodium bicarbonate as a buffer, lead to lower amounts of PEITC release (52% and 72% respectively).

Once the proper conditions were determined for the optimized release of PEITC from the treated seed, it was necessary to define those processing methods which would permit the greatest recovery of PEITC in a form suitable for industrial packaging. In order to have a dried plant product for encapsulation, the water from the treatment procedure had to be removed in such a way as to minimize the breakdown or loss of PEITC. Lyophilization to a final temperature of 26° C. led to non-detectable recoveries of PEITC within treated leaf tissues and only 31% recovery from treated seed meal as compared to similar samples which were not lyophilized. This recovery was increased to greater than 84% in treated seed meal, however, when the final temperature of lyophilization was decreased to 0° C., producing concentrations as high as 20 mg/g DW. The increase in the total PEITC content of these samples as compared to those reported in FIGS. 2–5 was due to the increase in the accuracy of the analytical methods which occurred during these studies. Leaf tissues lyophilized to 0° C. contained concentrations of nearly 195 $\mu$g/g DW of PEITC, but this concentration is nearly 100 times lower than found in the processed seed meal.

Lyophilized seed meal after treatment was kept at 22° C. in both open and closed containers in order to determine the stability of the PEITC within it. These experiments showed that both the open and closed treatments were very similar and contained an average concentration of 16.7 mg/g DW after 25 days which did not decrease significantly during that period. This concentration did decrease by an average of 18% after 68 days, but both of these samples were not protected from potential atmospheric hydration or oxidation. In general, the PEITC content of the treated seed meal appeared to be stable over extended periods of time.

References

Chen C-W, Rosen RT, Ho C-T (1998) Analysis and thermal degradation products of allyl isothiocyanate and phenethyl isothiocyanate. Pp 152–163 in: Challenges in the Isolation and Characterization of Flavor Compounds (Eds. C J Mussinan, M J Morello, ACS Symposium Series 705, American Chemical Society, Washington D.C.

Fahey J W, Zhang Y, Talalay P (1997) Broccoli sprouts: an exceptionally rich source of inducers of enzymes that protect against chemical carcinogens. Proc Natl Acad Sci 94:10367–10372

Gil V, Macleod A J (1980a) Degradation of glucosinolates of *Nasturium offininale* seeds. Phytochemistry 19:1657–1660

Gil V, MacLeod A J (1980b) Some glucosinolates of *Farsetia aegyptia* and *Farsetia ramosissima*. Phytochemistry 19:227–231

Gil V, Macleod A J (1980c) Studies on glucosinolate degradation in *Lepidium sativum* seed extracts. Phytochemistry 19:1369–1374

Hecht S S, Chung F-L, Richie J P, Akerkar S A, Borukhova A, Skowronski L Carmella SG (1995) Effects of watercress consumption on metabolism of a tobacco-specific lung carcinogen in smokers. Cancer Epidemology, Biomarkers, and Prevention. 4:877–884

Mithen R (1992) Leaf glucosinolate profiles and their relationship to pest and disease resistance in oilseed rape. Euphytica 63:71–83

Palaniswamy U, McAvoy R, Bible B (1997) Supplemental light before harvest increases phenethy isothiocyanate in watercress under 8-hour photoperiod. HortScience 32: 222–223

Virtanen AI (1964) Studies on organic sulfur compounds and other labile substances in plants. Phytochemistry 4:207–228

Wiley Registry of Mass Spectral Data. 6th edition with structures, Copyright 1994 by John Wiley and Sons, Inc.

Zhang Y, Talalay P, Cho C-G, Posner G H (1992) A major inducer of anticarcinogenic protective enzymes from broccoli: isolation and elucidation of structure. Proc Natl Acad Sci 89:2399–2403.

Zrybko C L, Fukuda E K, Rosen R T (1997) Determination of glucosinolates in domestic and wild mustard by high-performance liquid chromatography with confirmation by electrospray mass spectrometry and photodiode-array detection. Journal of Chromatography 767:43–52

The present invention is not limited to the embodiments described and exemplified above, but is capable of variation and modification without departure from the scope of the appended claims.

What is claimed is:

1. A nutraceutical composition comprising macerated plant seeds, said macerated plant seed preparation comprising phenethylisothiocyanate (PEITC) in an amount of at least 2 mg PEITC per gram fresh weight of the plant seed preparation.

2. The nutraceutical composition of claim 1, comprising at least 5 mg PEITC per gram fresh weight of macerated plant seeds.

3. The nutraceutical composition of claim 1, comprising at least 10 mg PEITC per gram fresh weight of macerated plant seeds.

4. The nutraceutical composition of claim 1 wherein said plant seeds are wintercress (*Barbarea verma*) seeds.

5. The nutraceutical composition of claim 1, wherein the plant seeds are fresh or fresh-frozen.

6. The nutraceutical composition of claim 1 wherein said preparation comprises 3 mg of PEITC per gram fresh weight of the plant seed preparation.

7. The nutraceutical composition of claim 1 wherein said preparation comprises 4 mg of PEITC per gram fresh weight of the plant seed preparation.

8. A method of obtaining a nutraceutical composition comprising a preparation of macerated plant seeds, the method comprising the steps of:

(a) providing seeds of a plant;

(b) disrupting the seeds to provide macerated plant seeds;

(c) incubating the macerated plant seeds in an aqueous solution at temperatures of 20° C. to 37° C. for at least two minutes; and (d) recovering a preparation comprising phenethylisothiocyanate (PEITC) in an amount of at least 2 mg PEITC per gram fresh weight of the macerated plant seeds.

9. The method of claim 8, wherein the macerated plant seeds in step (c) are incubated in water.

10. The method of claim 8, wherein the macerated plant seeds in step (c) are incubated in a buffer.

11. The method of claim 8, wherein the pH of the aqueous solution containing macerated plant seeds in step (c) is between 4.0 and 8.0.

12. The method of claim 8, wherein the pH of the aqueous solution containing macerated plant seeds in step (c) is between 4.5 and 7.2.

13. The method of claim 8, wherein the pH of the aqueous solution containing macerated plant seeds is about 7.2 when the incubation is conducted at 22° C. and about 4.5 when conducted at 30° C.

14. The method of claim 8, wherein the incubation is performed at a temperature between 22° C. and 37° C.

15. The method of claim 14, wherein the incubation is performed at a temperature between 27° C. and 32° C.

16. The method of claim 15, wherein the incubation is performed at 30° C.

17. The method of claim 8, wherein the incubation is performed for between 10 and 40 minutes.

18. The method of claim 17, wherein the incubation is performed for 20 minutes.

19. The method of claim 8 wherein said plant seeds are wintercress (*Barbarea verma*) seeds.

20. The method of claim 8, which further comprises freezing the plant seeds in liquid nitrogen before disrupting it.

21. The method of claim 8, which further comprises freeze-drying the preparation.

22. The method of claim 21, wherein the preparation is freeze-dried to a final temperature of 10° C. or less.

23. The method of claim 22, wherein the preparation is freeze-dried to a final temperature of about 0° C.

24. The composition recovered in step (d) of claim 8.

* * * * *